(12) United States Patent
Rogers

(10) Patent No.: US 7,771,341 B2
(45) Date of Patent: Aug. 10, 2010

(54) ELECTROMAGNETIC BRAIN ANIMATION

(76) Inventor: William Thomas Rogers, 3614 Hunters Cir., San Antonio, TX (US) 78230

( * ) Notice: Subject to any disclaimer, the term of this patent is extended or adjusted under 35 U.S.C. 154(b) by 1991 days.

(21) Appl. No.: 10/627,286

(22) Filed: Jul. 24, 2003

(65) Prior Publication Data

US 2004/0143300 A1    Jul. 22, 2004

Related U.S. Application Data

(60) Provisional application No. 60/441,610, filed on Jan. 22, 2003.

(51) Int. Cl.
*A61N 2/00*     (2006.01)
(52) U.S. Cl. ......................................................... 600/9
(58) Field of Classification Search ................ 600/9–15
See application file for complete search history.

(56) References Cited

U.S. PATENT DOCUMENTS

| | | | | |
|---|---|---|---|---|
| 5,092,835 A | * | 3/1992 | Schurig et al. | 600/9 |
| 5,738,625 A | * | 4/1998 | Gluck | 600/9 |
| 6,179,771 B1 | * | 1/2001 | Mueller | 600/13 |
| 7,010,351 B2 | * | 3/2006 | Firlik et al. | 607/45 |
| 2005/0228209 A1 | * | 10/2005 | Schneider et al. | 600/13 |
| 2008/0045865 A1 | * | 2/2008 | Kislev | 601/3 |

* cited by examiner

*Primary Examiner*—John P Lacyk

(57) ABSTRACT

This invention pertains to apparatus methodology formulated to perform electromagnetic brain animation (EBA) for the purpose of partial or complete alleviation of specific mental impairments relating categorically to infant, early childhood, and adolescent target populations. EBA expressly refers to an original system and mechanized manner for determining and redirecting particular areas of the brain found to suffer from endemic and/or environmental injury. Electromagnetic brain animation is an enhanced initiative for positive influence on brain region neuron activity with the impetus to habilitate, rehabilitate and/or redirect dysfunctional cellular structure in direct correlation with greater pliability of evolving nervous systems in conjunction with superior biological plasticity due to specified group cluster. The EBA technical inclination, evolution and fruition of "animation" are specifically related to safety and success with early developing brains. Special areas targeted, but not limited to, include depression, dysthymia, attention deficit disorder, learning disability, memory loss, overanxious disorder, mild retardation, and autism.

11 Claims, 11 Drawing Sheets

ELECTROMAGNETIC BRAIN ANIMATION

BACKGROUND OF INVENTION

Figure 1:
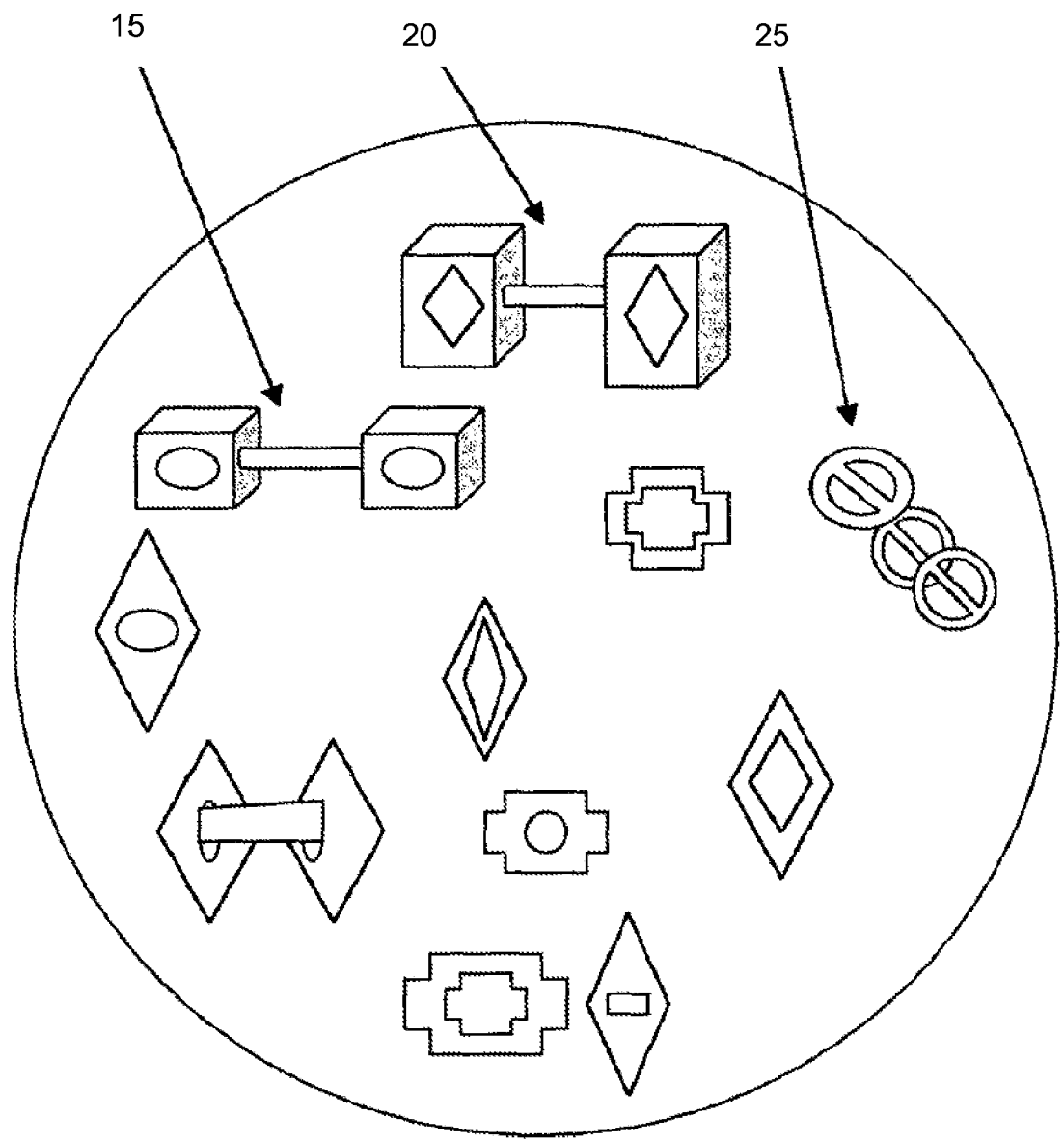

This invention relates to an original method for non-invasive brain stimulation using a magnetic field. The earliest nomenclature is transcranial magnetic stimulation (TMS).

TMS is based on the principle of electromagnetic induction, whereby the cerebral cortex is stimulated as an outcome of the rapid discharge of current through a coil held over the scalp. This discharge induces an electric field surrounding the coil, which in turn induces current flow of a sufficient magnitude to depolarize and/or stimulate neurons in underlying tissue. The basic principle relates to cell membranes sustaining potential difference between intra- and extra-cellular space. An externally applied electric field may deviate the cell's membrane potential; that is, depolarize the membrane and hence activate excitable tissue. Electric fields suitable for neural stimulation can be generated non-invasively by applying electromagnetic induction. At this point, a majority of TMS research and treatment has been limited to the stimulation of the motor cortex area due to discernible effects being relegated only to that general locale. There are also a number of treatment and procedure difficulties relating to such areas as patient compatibility, discerning exact application, possibility of multiple action modalities, rationale of device, and most amenable target population.

Transcranial magnetic stimulation has been studied at precise and considerable length for at least the past 15 to 20 years; initial modern demonstrations by Barker, et al., in Sheffield, England, in 1985. (Origins of modern study—1960s,—Early concept formulation late 1800s) There has been improvement coming from several directions during the last 10 years. TMS did shift from continued research and theoretical investigation to actual application within specific and basic perimeters. A significant upgrade pertains to rapid transcranial magnetic stimulation (rTMS)—approximately one pulse every 0.10 to 0.50 seconds—involving using a figure-8 surface coil (a stimulating coil with two planar wings with opposing current directions; induces a better focused electric field than a single circular coil as was previously used) formulation in the mid 1990s and has been brought into play with the goal of treating the cognitive dysfunction of has been brought into play with the goal of treating the cognitive dysfunction of depression (George et. al., the Journal of Neuropsychiatry and Clinical Neurosciences, 8.373, 1996. Kolbinger et al., Human Psychopharmacology, 10:305, 1995).

TMS has several present and potential applications, in the domains of basic neuroscience research and of the treatment of brain disorders. Currently TMS delivery system and/or technique is rather rudimentary. The TMS stimulator is a wire-wound coil, typically shaped like a "B." The B-shaped coil is placed against the scalp and held in place by a human clinician. This causes geographic and stability problems for both the patient and clinician. For the primary motor cortex and primary visual cortex (small sections of the total brain surface), proper positioning is established by the elicited response: muscle contractions when stimulating the primary motor cortex; illusory lights (phosphenes) when stimulating the primary visual cortex. In both of these areas, the effects are very sensitive to coil position and orientation. Many times false or skewed readings are the result. This, of course, makes utilization non-pragmatic, generally speaking. A more dependable method for determining the proper position and orientation of TMS coil position for brain areas deficient in immediately observable feedback is something that is required for further movement forward.

Of late (past 5-8 years) there has been a considerable increase related to multiple investigations of TMS potential toward at least some partial alleviation of cognitive dysfunction related to depression.

A. Barker A T, Jalinous R, Freeston I L. (1985) Non-invasive magnetic stimulation of human motor cortex. Lancet 1106-1107
B. George et. al., "Transcranial Magnetic Stimulation: A Neuropsychiatric Tool For The 21.sup.st Century," J. Neuropsychiatry, vol. 8, No. 4:373-382 (1996).
C. Kolbinger H M, Hoflich G, Hufnagel A et al. (1995) Transcranial magnetic stimulation (TMS) in the treatment of major depression: a pilot study. Human Psychopharmacology 10: 305-310.

OTHER REFERENCES

1. Geller V, Grisaru N, Abarbanel J M, Lemberg T, Belmaker R H. Slow magnetic stimulation of prefrontal cortex in depression and schizophrenia. Progress in Neuropsychopharmacology and Biological Psychiatry 1997; 21:105-10.
2. M. E. Keck et al., "Neuroendocrine And Behavioral Effects Of Repetitive Transcranial Magnetic Stimulation In A Psychopathological Animal Model Are Suggestive Of Antidepressant-Like Effects," Neuropsychopharmacology, vol. 24, No. 4: 337-349 (2001).
3. T. A. Kimbrell et al., "Frequency Dependence Of Antidepressant Response To Left Prefrontal Repetitive Transcranial Magnetic Stimulation (rTMS) As A Function Of Baseline Cerebral Glucose Metabolism," Biol. Psychiatry, 46:1603-1613 (1999).
4. H. M. Kolbinger et al., "Transcranial Magnetic Stimulation (TMS) In The Treatment Of Major Depression—A Pilot Study," Human Psychopharmacology, vol. 10: 305-310 (1995).
5. Conca A, Koppi S, Konig P, Swoboda E, Krecke N. Transcranial magnetic stimulation: a novel antidepressant strategy? Neuropsychobiology 1996; 34:204-7.
6. S. H. Lisanby et al., "Magnetic Seizure Therapy Of Major Depression," Arch Gen Psychiatry, vol. 58: 303-304
7. Pascual-Leone A, Rubio B, Pallardo F, Catala M D. Rapid-rate transcranial magnetic stimulation of left dorsal lateral prefrontal cortex in drug resistant depression. Lancet 1996; 348:233-7.
8. S. J. Norton, Can ultrasound be used to stimulate nerve tissue. BioMed Engineering Online 2003; 2 (1): 6.

BRIEF SUMMARY OF INVENTION

Electromagnetic brain animation (EBA) is a transformative initiative for positive non-invasive influence of brain region neuron activity in direct correlation with superior integration advantages of target treatment population. This invention not only adds a multiplicity of innovative enhancements to the basic idea of neural stimulation using a magnetic field; it formulates original apparatus mechanisms toward practical application within special chronological borders. A wide variety of mental processes are known to be initiated, controlled and/or influenced by neural activity in particular regions of the brain. During infancy, early childhood and adolescence, assistance with habilitation, rehabilitation and/or redirection of nervous system normal and dysfunctional growth is inestimably more practically feasible due to unique cellular plasticity and early development formulation. EBA process, indicator specifications, technical inclination, and intentioned group cluster are singular innovations, which relate directly to an advanced pragmatic approach for partial alleviation or fill acquiescence of multiple cognitive dysfunctions. Electromagnetic brain animation (EBA) is a new phraseology now entered into the neuroscience lexicon. The majority mechanistic instrumentation relating specifically to EBA sits comfortably upon the patient's head in the broad form description of a hat-like device. Thus, the secondary, colloquial nomenclature of said invention is "The Thinking Cap".

Advantages of this invention include but are not limited to>(a) Complementary utilization with ultrasound specifically regarding target population of infant, early childhood, to adolescence. (b) Particular and specific regions able to be influenced by animation, exclusively unto EBA, and also additionally with the potential for dual modality ultrasound. (c) Superimposed magnetic fields from multiplicity 100+ mini-coils. (d) Multiple variations in coil formulation, physicality, and/or structure/contour. (e) Current amplitude, pulse repetition rate, Hz gradient, i.e., all induction immersions controlled individually from outside, separate control box centers. (f) "Cap" and/or hat-like instrumentation contained device fixated and stable on/over patient head wherein all coils (100+), directional formulations, multiple configurations, et., al., are integrated as continual functioning particulars elevated off skull approximately minimum one half inch relating to moveable/flexible padded prong contact points integrating structure and architecture of cap/hat. (g) Cap/coils elevation from skull can be/is variable via adjustable prongs. This ability has positive impact on focus of magnetic fields. (h) Specific coil placement inside and target plotting precisely possible from multiple stated "cap" locations via coverage front to eye brow area, back to nape of neck, sides to top of ear level.

Specific instrumentation and/or services advantages include, but are not limited to,>Acceptance incorporation of "animation" vs. forced merging of "stimulation". The upgrading and sophistication of "animation" is due to formulation of EBA's "composite amalgamation" (multiple coil inductions, numerous locales, frequent variations, varied distance, rotating transmissions, multiple combined correlations thereof) excitation impetus toward assisting influence of target rather than singular more sharply rigorous induction toward forceful manipulation of same region. Beyond this innovative assemblage, there is the added archetype potential for corresponding utilization of ultrasound in conjunction with, or as a primary, for any type of brain nerve excitation (particularly when relating to early developing brain dysfunction, "excitation" can be a bit of a misnomer—not actually meaning to make more dynamic, but to make different, to sometimes make less dynamic). This is due, for example, to the fact that a number of early childhood cognitive dysfunctions, i.e., autism, ADD, and overanxious disorder seem to be initially manifested in the first place because of "over excitation" of neuron activity. Also included with instrumentation is the modernity of a curved (head contoured) conductive malleable plate situated against the inner top of the "cap" which can be utilized to connect two or more of the smaller coils transmission as one for a single stronger focused field in accord with the size of the combined coils. This all-inclusive integration of EBA is more attuned toward safety with intended milieu of early childhood developing brains. In addition, EBA is an "adaptor modality shifter". That is to say, "The Thinking Cap" has the capability to fit "extra low" output emissions, via a mobile battery hookup, (XLEBA) as well as urtra rapid output (urEBA) and the aforementioned ultrasound interactivity which relates to the acronym EBA/us.

Continued advantage facets of the invention are that treatment modus operandi offer the possibility to probability of several DSM V category illness alleviations and/or improvements at a lower financial expenditure and greater broad-based acceptance of at-risk and "special" populations than at any time previous relating specifically to intellectual enhancement possibilities for mentally impacted early childhood clusters and/or groupings. Applications of this new EBA methodology includes the prospective for improving the condition of individuals with cognitive disorders, such as dysthymia, attention deficit, learning disorder, overanxious disorder, panic disorder, separation disorder, and mild retardation, as well as potential for help in areas such as memory loss, depression, obsessive-compulsive disorder, and some behavior disorders. Overall, this is a comparative short term, in-office, non-intrusive, non-invasive, painless, inexpensive, brief per session, easily tracked, readily redirected and/or corrected, procedure which coalesces into a comfortable, not unpleasant experience.

Due to wholly inclusive change in instrumentation, process, sophisticated and refined induction, differentiating magnetic field coagulation, multi-control based individual connections, animation of superior particle fields, unilateral coil augmentation variation, potential pairing integration with ultrasound, and target population; electromagnetic brain animation (EBA) has elevated potential and enhanced probability for notable assurance in corrective neuro-habilitation, rehabilitation, and redirection heretofore not available, specifically within the age barriers of early childhood development.

BRIEF DESCRIPTION OF SEVERAL VIEWS OF DRAWINGS

FIG. 1—is a view of inside of EBA "Thinking Cap" which fits elevated over the patient's head previous to treatment. There are 100+ varying sized induction contact points positioned within for direct over-head brain region assimilation purposes. The shape of generated electric fields are basically dependent on three factors: 1. Shape of the induction coil. 2. Location and orientation of coil with respect to cranium and/or brain (regions). 3. Electrical conductivity/structure of brain tissue. The earliest simplest shaped coils are circular ones. Basic round coils are comparatively powerful, but they have a much larger focal point than any of the more modern shaped coils related to EBA; which elicit a specificity of focus not achieved by earlier coil models.

Figure 2:
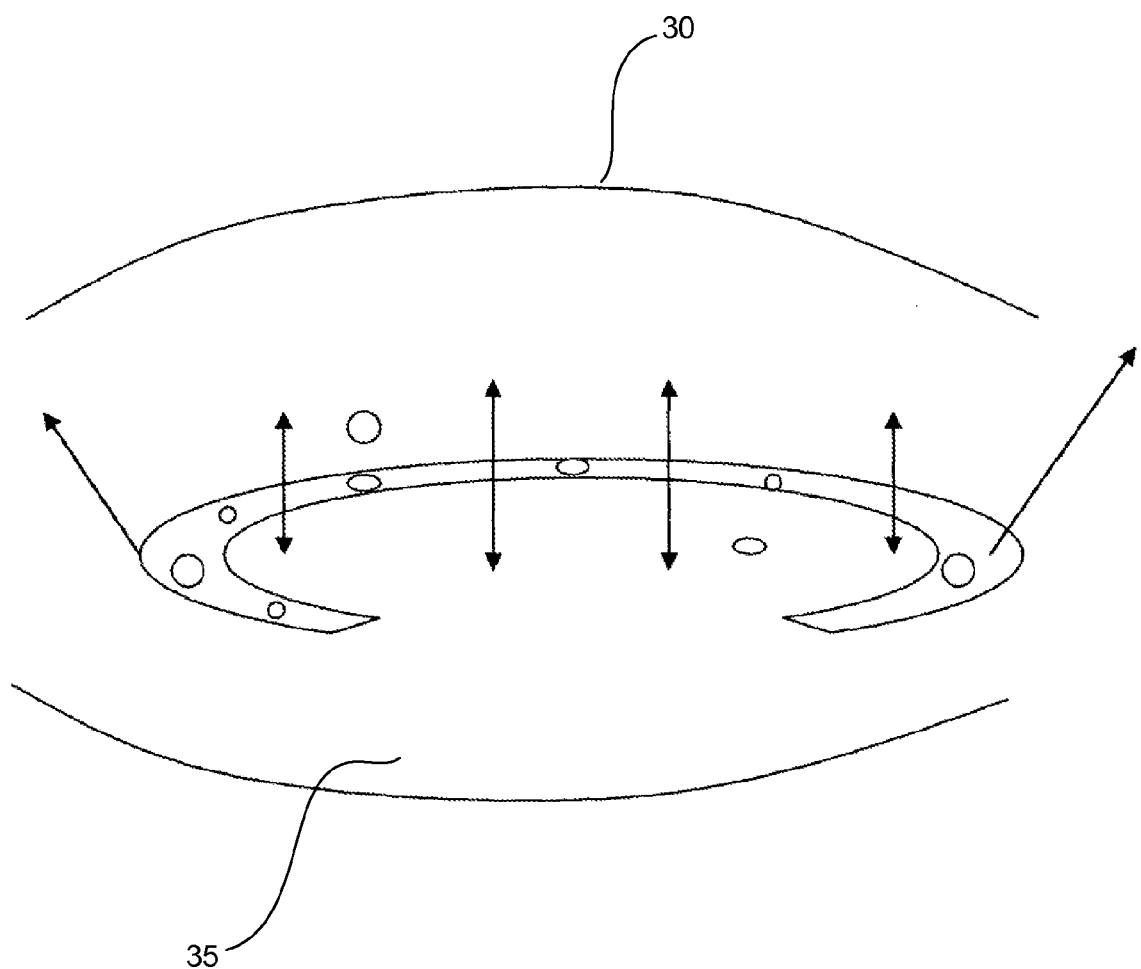

FIG. 2—Is the adjustable "plate"—circumventive within the "cap" one half/three quarters above the contact, electrode, fixated coils, and around the skull area. The plate is a pliable conductive material about one eighth of an inch in thickness bent in the basic underneath shape of "The Thinking Cap". The purpose is to be able to increase the emission field of two or more of the small coils by connecting the output of those two or more via the "conducting plate". This is achieved by contact of those two or more coils actually with the "plate".

Figure 3:
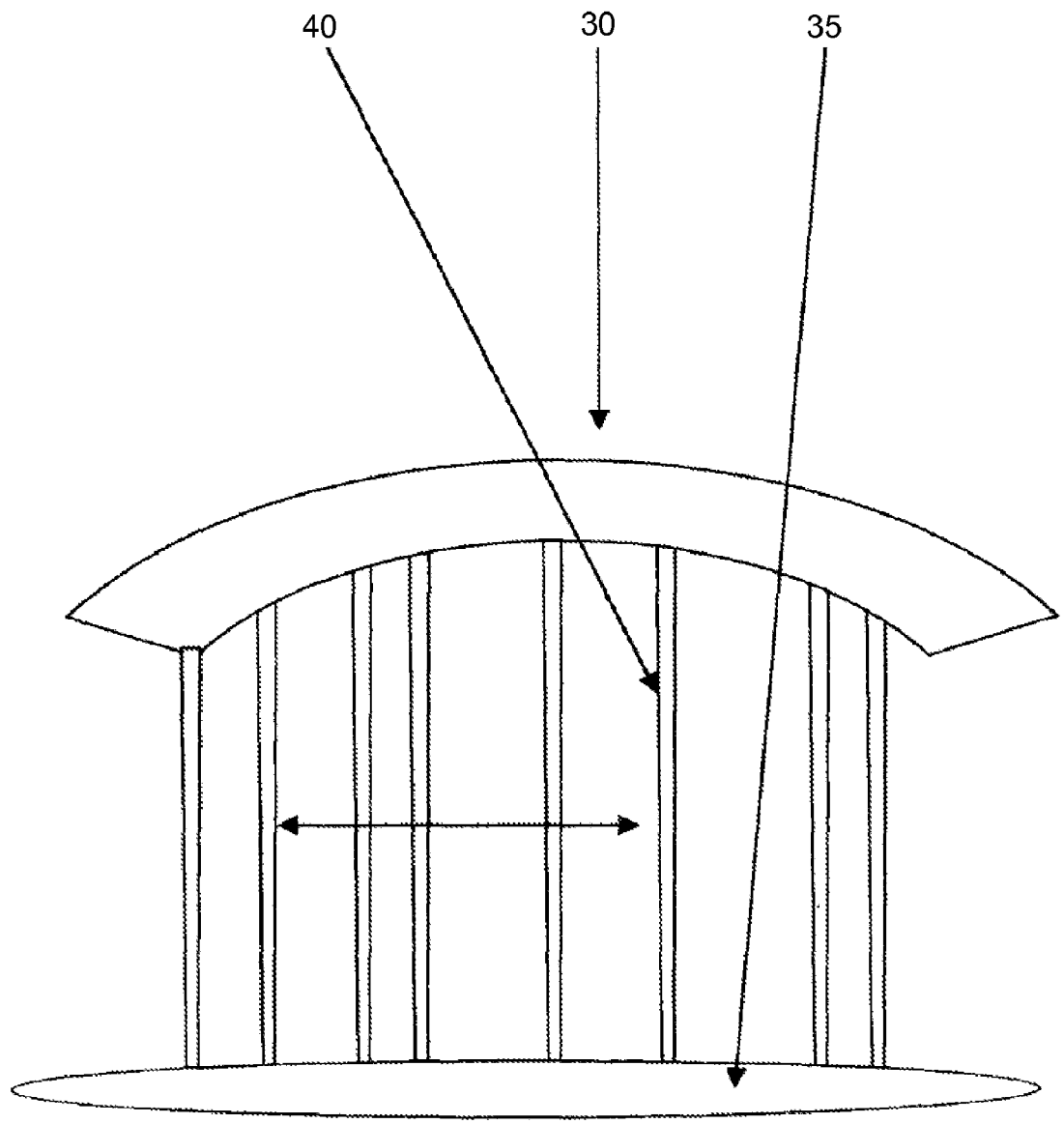

FIG. 3—Are the "prongs", moveable/adjustable, by which "The Thinking Cap" is fixated and situated on the patient's head previous to treatment. There are anywhere from 7 to 12 prongs. They are pliable and padded for comfort to the head. Adjustability distance of coils from skull can range from one half to 3-5-7 inches.

Figure 4:
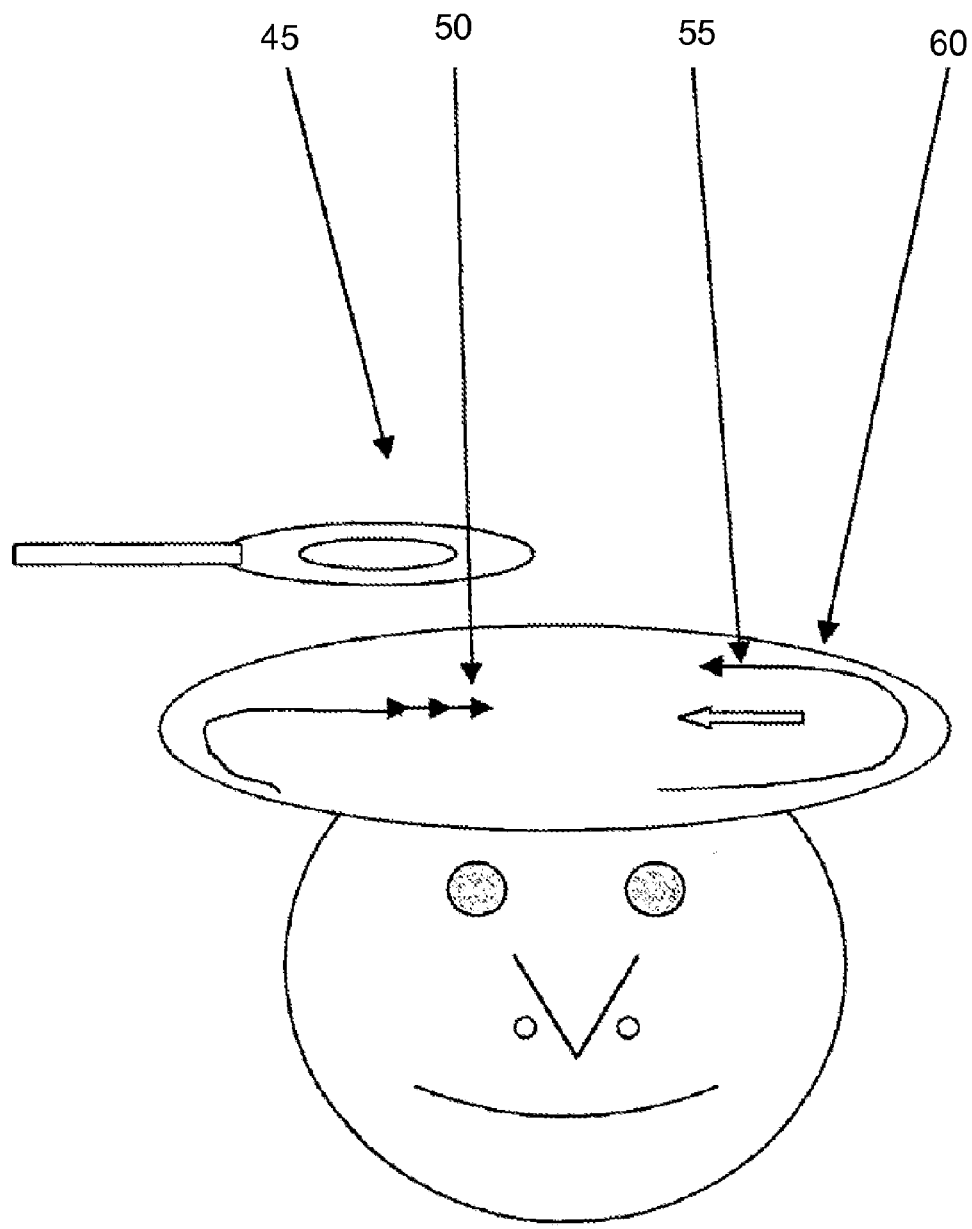

FIG. 4—Is illustration of phenomenon of directional specificity>a single coil at the vertex can stimulate tissue on either side of the brain according to the direction of the current inside. The image shows basic current flow in singularity with induced currents from a circular coil one up with the preferred animation directions of motor cortex. The inclusive multiple power wires cord flows from top cap integration points connected to inside coils inside cap—100 plus. These wires condense into one capable, insulated cord for male induction into power source (s). Illustration also power transmission wiring from top of "Cap" to multiple (one or more) power sources depending on treatment at time. Numerous source boxes/table instrumentation may be involved.

Figure 5:
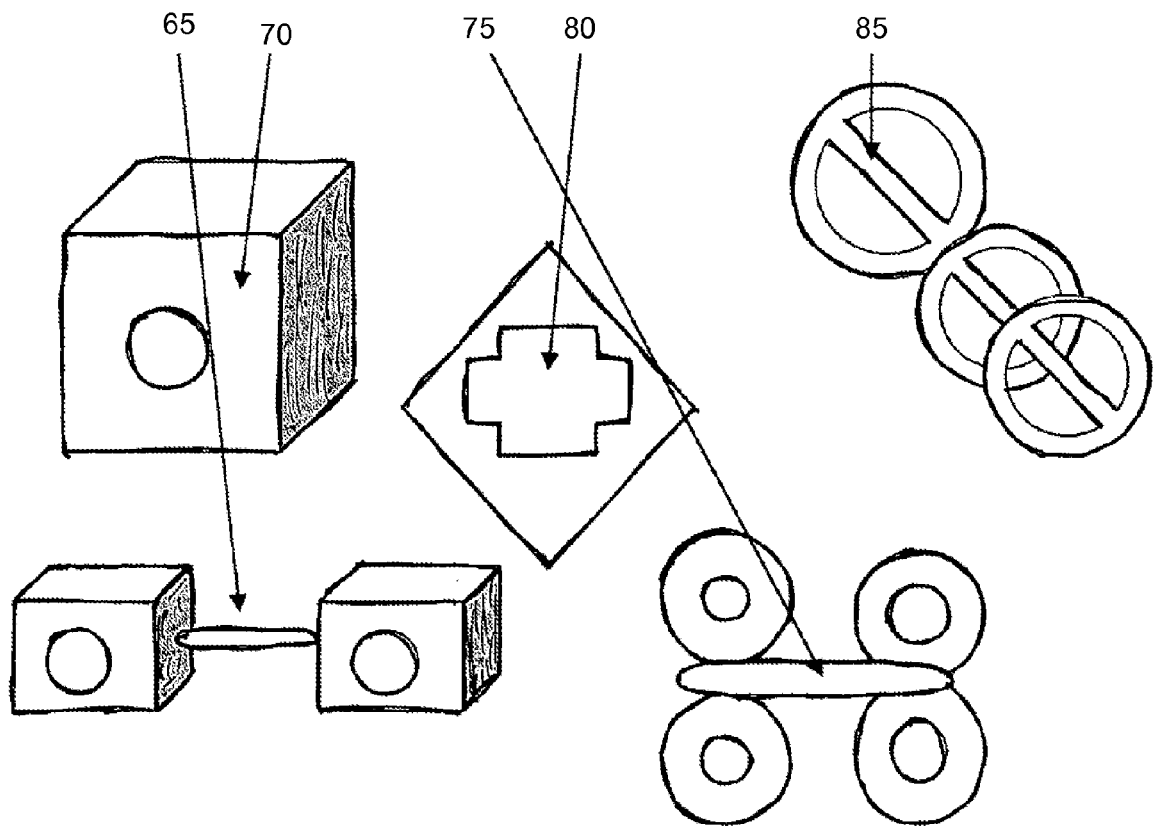

FIG. 5—shows multiple EBA coils in varying configurations. With standard induction, the simplest shaped coil is a circular one. Round coils are comparatively powerful but also have a relatively large focal area. The "triple bar circle" or the "double figure-of-eight" or the "dumbbell" coils shown here all emit a stronger, more specific and useful focus field than previous coils. Other coils shown are variations of same theme. Newer versions of these coils which are filled with iron use only about a quarter of the power of normal coils, and produce only a fraction of the heat. The "double squared circle" and "double rectangled triangle" are only two of several coil shapes utilized only with EBA (electromagnetic brain animation). The production of heat may be cut several fold due to formulation. These potential conclusions are precisely apropos for our specific early childhood target population.

Figure 6:
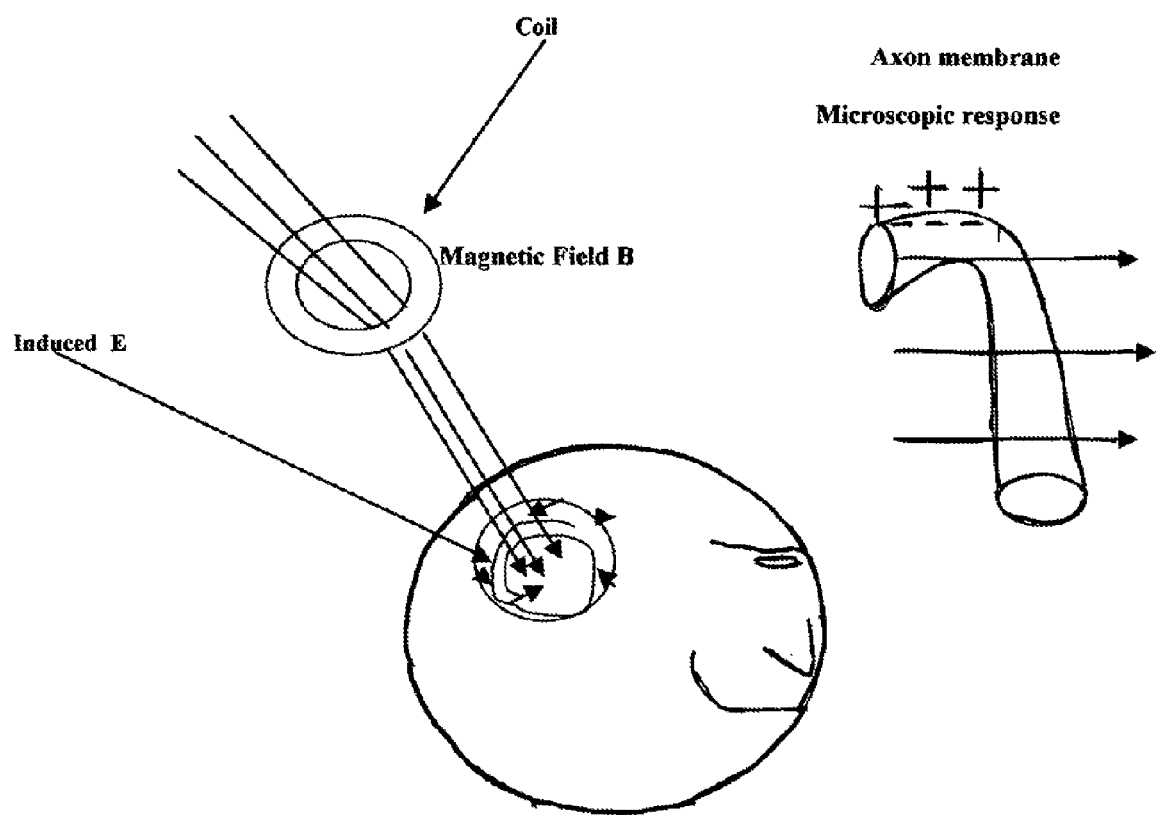

FIG. 6—Summarizes the basic chain of events in EBA. The induced E is strongest near the coil and typically stimulates a cortical area of a few centimeters in diameter. EBA pulses cause coherent firing of magnetic fields formulations in the animated area as well as altered multiple firings to synaptic input, i., e., neurotransmitter-receptor clusters. At microscopic level, E affects the nerve cells' transport voltage across brain region membrane and thereby the voltage-sensitive ion channels. Complementary brain imaging tools are used to detect the associated electrical currents and changes in blood flow of metabolism.

Figure 7:
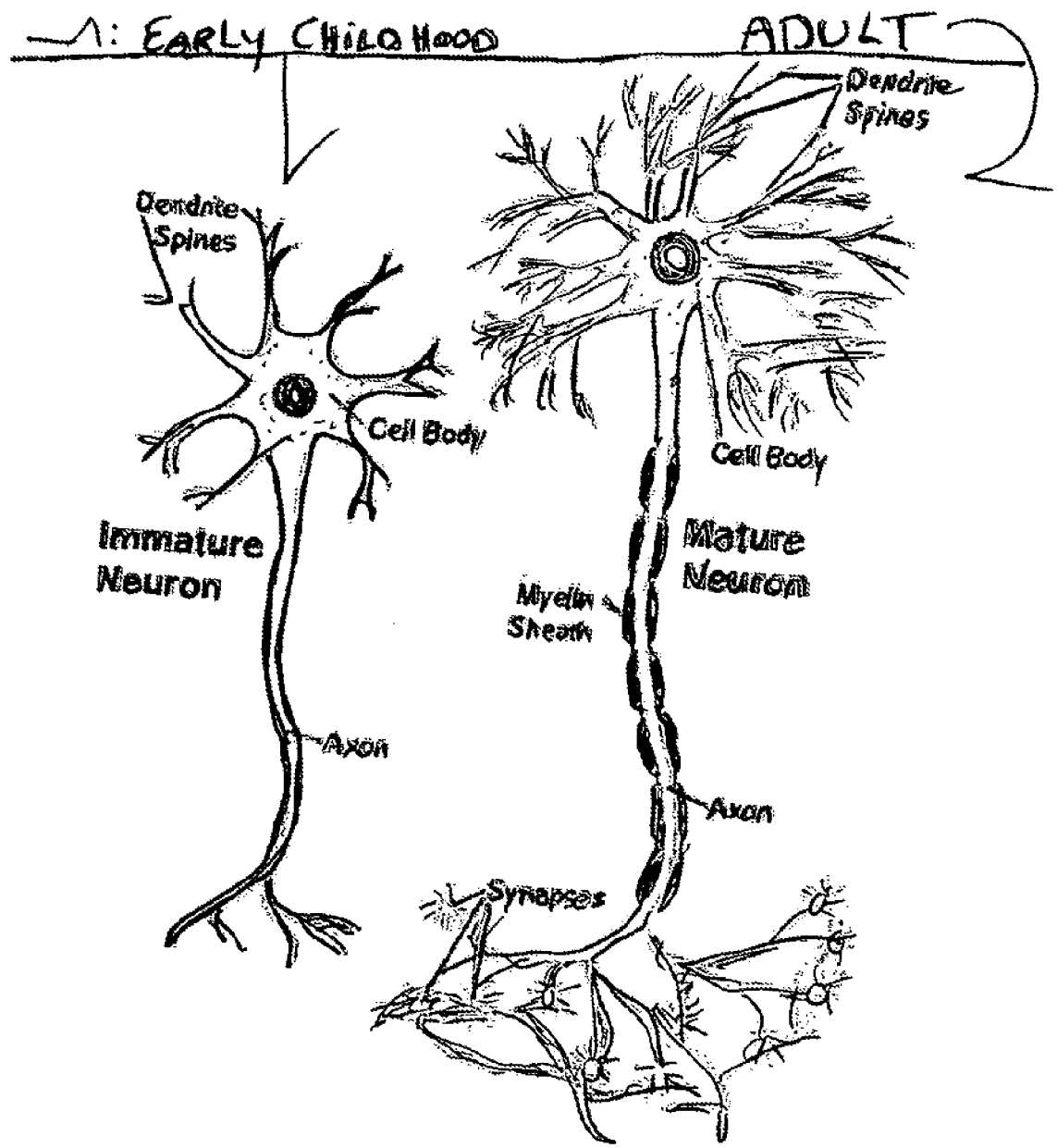

FIG. 7—Shows differentiation between early childhood—during critical and sensitive opportunity for intervention and/or extraordinary opportunity for learning. EBA target bombardment with accentuated electric fields via multiple varying densities, Hz, pulsations, watts, amps, coordinated waves and/or waves of induction, and potentially (in specific cases) parallel sonic integration may prompt typical growth or redirect and/or enable abnormal growth. Critical periods represent a narrow window of time during which the brain is most vulnerable to the absence of stimulation or to environmental influences. Sensitive periods are the broad windows of opportunity for certain types of learning. Sensitive periods represent a less precise and often longer period of time when skills, such as acquiring a second language, are influenced.

Figure 8:
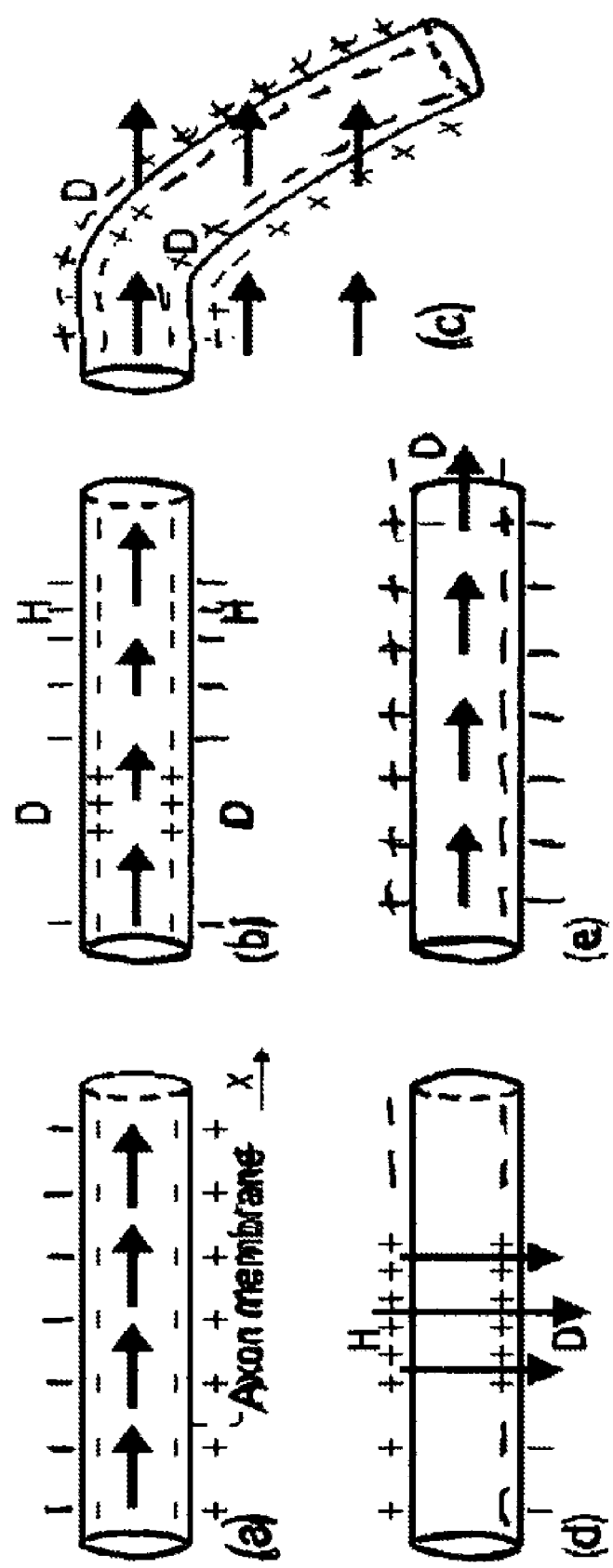

FIG. 8—Relevance to axons, the ratio of transverse and gradient field mechanisms are independent of the axon size. A drawing shows activation mechanisms and axon membrane polarization in a transverse field is shown for varying external applications of electric field patterns. Inherent implication is given that E (the electric field) is indistinguishable outside and inside of cellular structure.

Figure 9:
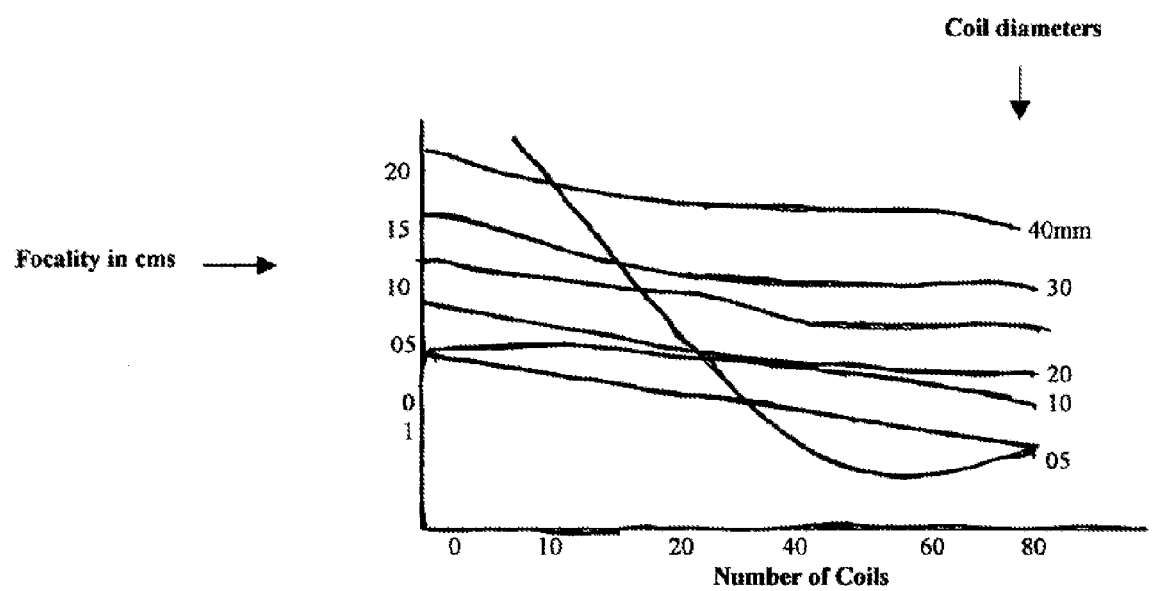

FIG. 9—Refers to use of multiple independently controlled animating coils. It has any number of advantages of over standard one coil or figure-of-eight coil stimulation. One can excite/animate numerous loci at the same time, or at delaying or varying times. With EBA, the operator can concentrate two or more coils at one locations and/or multiple location with any number of cross configurations. In addition, the smaller the coils in combination with the multiplicity of coils relates directly to the size and specificity of the focality of animation induction.

Figure 10:
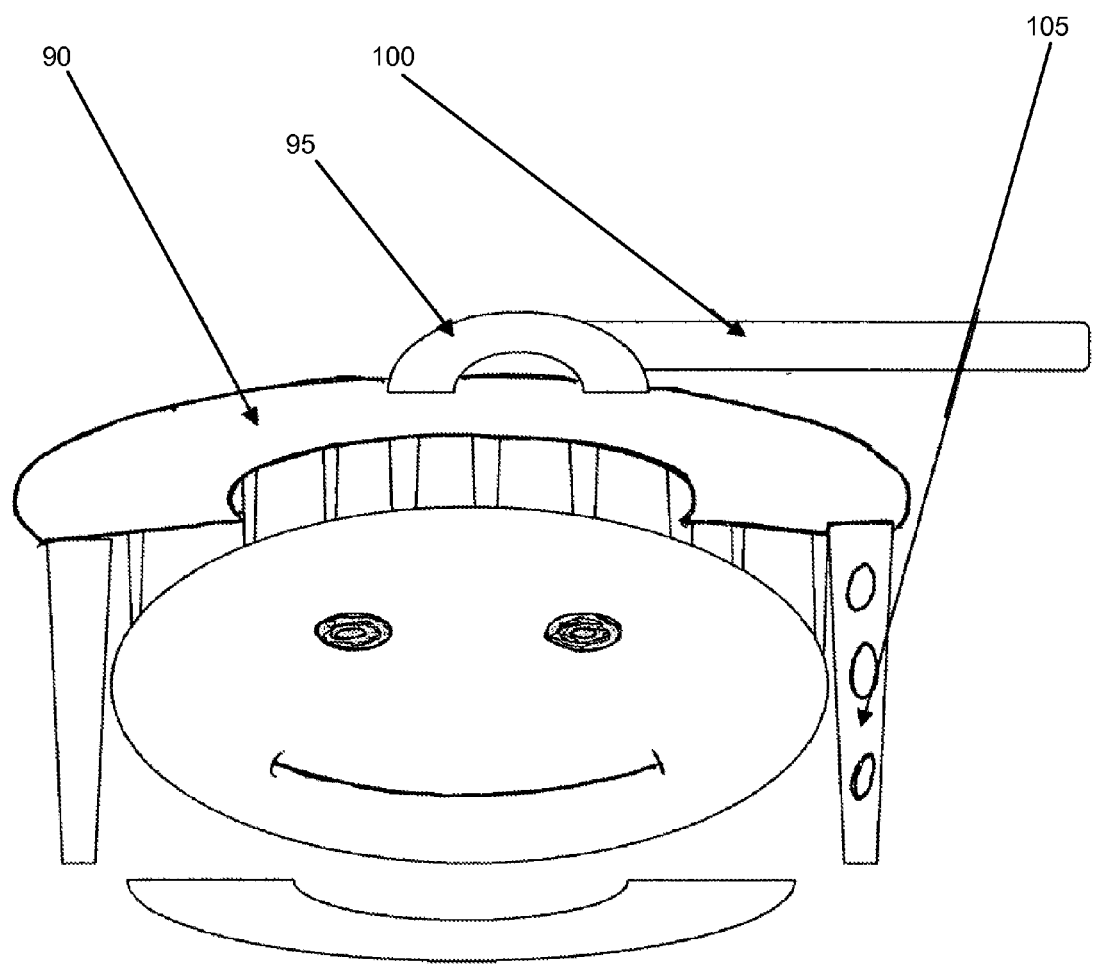

FIG. 10—Refers to outside view of "The Thinking Cap" instrumentation of the electromagnetic brain animation generator. Also shown in part are adjustable "prongs" that allows a variation in distance of coils from skull. It is a hat/helmet-like device sturdy enough and spacious enough to allow all necessary inclusive mechanisms. Relating to the ultrasound attachments, validation of localized stimulation of active (nerve or cortical) tissue by ultrasonically induced electric fields relates directly toward analytical solutions pertaining to the field distribution which can be derived for an ideally collimated (parallel) ultrasonic beam.

Figure 11:
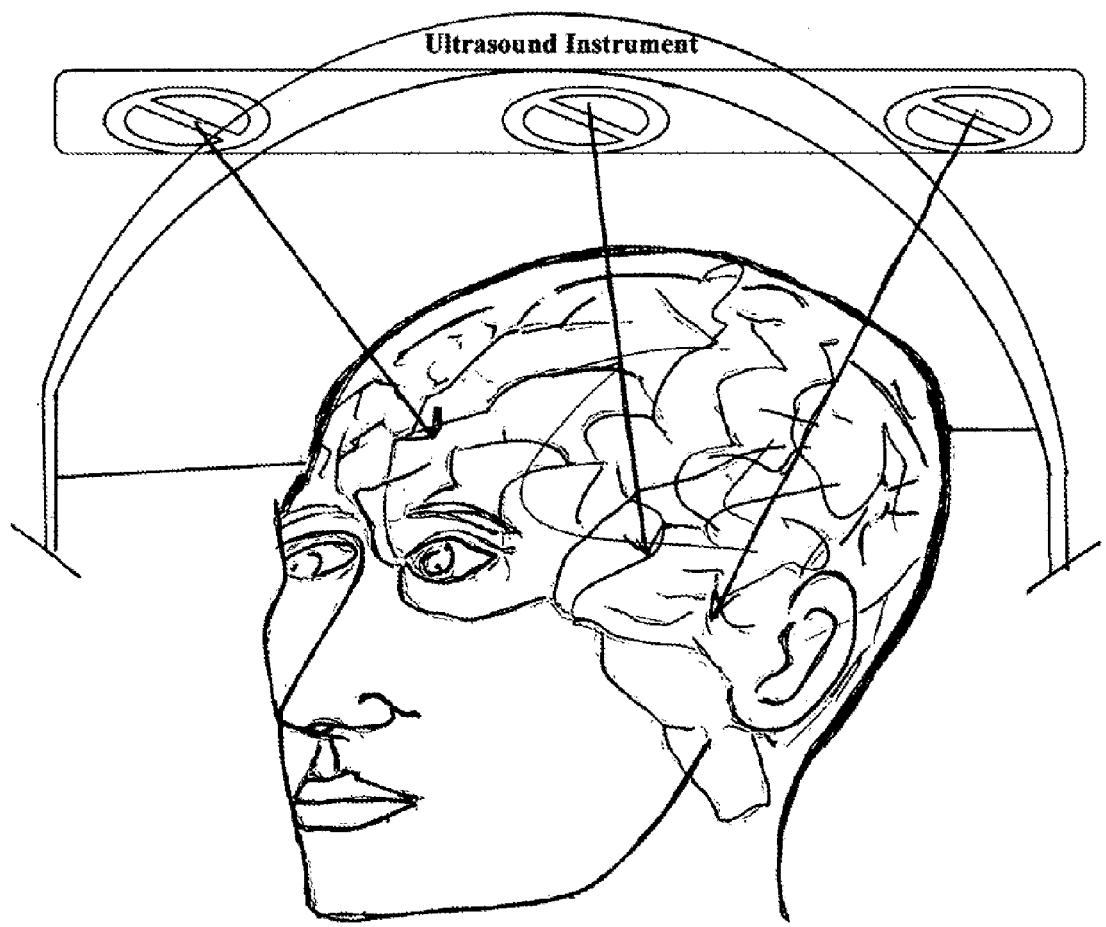

FIG. 11—Shows the initial treatment modality relating to EBA/US whereas ultrasonic waves vibrating at frequencies greater than 20,000 cycles per second, i.e., beyond the range of human hearing, are integrated through the human/patient's skull and into an excitation focal area (in this case the "limbic system" due to manifestation of "overanxious disorder"). The sonographic induction causes initial 1st phase animation to enmesh targeted organicity bringing multiple neuron structure to hypersensitive pre-threshold status. Immediately after goal achievement, exclusive EBA utilizing full "Thinking Cap" instrumentation begins final and conclusive successful animation of "sonically prepared" brain region.

DETAILED DESCRIPTION OF THE INVENTION

Electromagnetic brain animation (EBA) is a heretofore unparalleled and enhanced initiative for positive non-invasive animation of brain region neuron activity in correlation with superior biological plasticity and period cellular development related specifically and only to early childhood target population. A wide variety of mental processes are now known to be initiated, controlled and/or influenced by neural activity in particular regions of the brain. This invention formulates original apparatus mechanisms toward practical application within these stated chronological borders. EBA process, mechanistic specifications, technical inclination, and intentioned group cluster are singular innovations. EBA relates directly to an advanced system and mechanized approach for determining via specific region locale, within the infancy to adolescence age category, optimum areas for magnetic field focus, and potentially habilitating, rehabilitating and/or redirecting particular areas of neurotransmitter brain activity and/or cellular dynamics which may be found to suffer from endemic and/or environmental injury resulting in cognitive dysfunction. Electromagnetic brain animation (EBA) is a new phraseology now entered into the neuroscience lexicon.

EBA is presented as a primary instrument relating directly to biological brain analysis specifically connected to the potential for improvement and/or alleviation of multiple cognitive dysfunctions. Unequivocally, EBA is further enhanced because the use of complementary non-invasive neuroimaging has increased explosively in recent years. Details of the functioning of the human brain are now revealed by measuring electromagnetic fields outside the head or metabolic and hemodynamic changes using electroencephalography (EEG), magnetoencephalography (MEG), positron emission tomography (PET), near-infrared spectroscopy (NRS) and functional magnetic resonance imaging (fMRI). These innovative and/or improved invention manifestations being a positive adjunct to electromagnetic brain animation also include TMS, which most basically and assuredly continues as a direct way of manipulating and interfering with the function of the cortex. EBA, conversely, is manifested explicitly as the primary instrument pertaining to and in correlation with high potential for acquiescence and/or alleviation of mental disabilities throughout infancy, early childhood, and adolescent development.

The continuing specificity of description relates directly toward a neuroscience, neuropsychological instrumentation.

An electromagnetic brain animation generator utilized expeditiously for the benefit of infant, early childhood, adolescent mentally dysfunctional populations (autism, depression, panic disorder, memory loss, conduct disorder, dysthymia, over anxiously disorder, and/or including, but not limited to, general organic cognitive dysfunction reference chemical neuron, electrical, magnetic malformation and/or malfunction within cerebral cortex, cerebellum, limbic system, brain stem, frontal, temporal, parietal, occipital lobes—inclusive of brain areas relevant to target population mental disabilities. A major part of the physicality of the instrument includes a device which is fitted over the head (cap) with multiple conducting pads located (coils) inside the hat/cap area for reception of main power sources, converting to electromagnetic pulse/power induction/variations which, when programmed and processed appropriately, will conclude in mild/moderate/significant improvement and/or complete acquiescence of multiple early developing mental disorders. Being that this stated early childhood cognitive dysfunction alleviation device coordinates its structural architecture toward human head encasement, the colloquial reference nomenclature has evolved as "The Thinking Cap".

An additional most significant complementary partnering instrumentation which is introduced the first time, especially and most specifically, relating to innovative patent presentation relates directly toward compound utilization of ultrasound. Generally speaking ultrasound or sonography is a technique that uses sound waves to study and treat hard-to-reach body areas. In scanning with ultrasound, high-frequency sound waves are transmitted to the area of interest and the returning echoes recorded. First developed in World War II to locate submerged objects, the technique is now widely used in virtually every branch of medicine. In obstetrics it is used to study the age, sex, and level of development of the fetus and to determine the presence of birth defects or other potential problems. Ultrasound is used in cardiology to detect heart damage and in ophthalmology to detect retinal problems. It is also used to heat joints, relieving arthritic joint pain, and for such procedures as lithotripsy, in which shock waves break up kidney stones, eliminating the need for surgery. Specifically speaking, "ultrasound" means—a frequency greater than 20,000 Hz, approximately the upper limit of human hearing Ultrasound is noninvasive, involves no radiation, and avoids the possible hazards—such as bleeding, infection, or reactions to chemicals—of other diagnostic methods. All of these indications allow ideal compatibility with goals and process of electromagnetic brain animation toward early developing brains.

A conjunctive method of animating cellular structure of the brain is an additional initial operative proposition of EBA. Especially in working with early childhood habilitation development, utilizing ultrasound, during specifically designated referenced criterion, along with exclusive electromagnetic brain animation to formulate inclusive EBA with ultrasound or EBA/us. At the highest electric fields, relating to ultrasound, the field strength availability may not quite be to the level of power generally associated with standard stimulation and/or animation. However, that particular capability strata is not mandated for our partnering complementary purposes. Ultrasound emanations are a wholly different constituency (physics-structure) than any energy source ever used as a primary or secondary for these stated designs. Brain neuron tissue can most assuredly be activated by ultrasound at its available electric field gradient level especially in the presence of an earlier initiated magnetic field induced by electromagnetic brain animation. For example, an ultrasonic pulse moving about in an electrolytic fluid (such as soft tissue) in the presence of a static magnetic field (partial, minor EBA initiation) oriented in a direction at a 90-degree angle to the "movement" path. The longitudinal particle motion due to the ultrasonic wave moves the ions back and forth through the magnetic field; this results in Lorentz forces (the force on a charged particle moving through a region containing both electric and magnetic fields) on the ions that give rise to an electric current density that oscillates at the ultrasonic frequency. This strongly relates to the conclusion that analytical solutions for the field distribution of ultrasonic wave pulsations most specifically can be coagulated toward an ideally collimated (parallel) ultrasonic beam. [As an example, an ion in a conductive medium with charge q. The longitudinal particle motion of an ultrasonic wave will cause the ion to oscillate back and forth in the medium with velocity v. In the presence of a constant magnetic field, $B_0$, the ion is subjected to the Lorentz force $F=qv \times B_0$. (1) This produces an electric current density given by $J_0=(n_+u_+ + n_-u_-) F$, (2) where $u_+$ and $u_-$ are the mobilities of the positive and negative ions (assumed to have charges of q and −q, respectively), and $n_+$ and $n_-$ are their concentrations. Combining (1) and (2) gives $J_0=q(n_+u_+ + n_-u_-)v \times B_0$.] This beam would act as a precursor, a preparation of specific designated nerve cells toward more sensitive and greater excitability and/or capacity for influence, concluding in positive, directive neuron persuasion by immediate follow-up introduction of full potency electromagnetic brain animation; thus, EBA/us. There is little doubt that, at the very least, pre-ultrasound integration would accentuate not only the ability to animate and potentially rehabilitate neuron activity but it would also assist with limited foci designations; that is to say, superior localization of desired site as well as deeper integration into the brain. Now entered into "field" lexicon/terminology is EBA/us.

At its optimum potential, the combining of ultrasound with EBA is an innovation of significant ↑prominence elevated to a level of equal distinction of participation with previously mentioned adjunct instrument toward nerve cell preparation. Again, the spatial and temporal integrity of the ultrasound "fields" are very different from those induced by magnetic induction. One such difference is that the wave variations of the ultrasonically-induced fields are much more rapid than the fields related with currently utilized stimulation. What this means is that the magnitude of the gradients of the electric fields produced by sonography can be comparable to those associated with currently utilized stimulation previous to EBA, i.e., TMS. This has strong importance due to recent understanding giving specified indication that not strength, but rather gradient of the field, is primarily responsible for neural excitation. Another difference and thus augmentation of ultrasonic stimulation relates to improved ability to control time dependence of an ultrasonic pulse due to its aforementioned distinctive structure. This makes it possible for one to transmit an ultrasonic pulse train at essentially any repetition frequency or modulate a continuous ultrasonic wave in a variety of ways. A point to again make, is that the ultrasonically-induced electric field gradients are comparable to typical currently utilized stimulation gradients previous to electromagnetic animation, because the ultrasonically-induced fields pass from maximum to minimum in a much shorter distance, i.e., approximately half the ultrasonic wavelength (a fraction of a millimeter). A second point to add is that one can exercise greater control over the temporal shape of the ultrasonically-induced electric fields compared to heretofore-induced fields. For example, the excitation can be oscillatory ("polyphasic") or not (approximately "monophasic," with a sharp up-going excursion followed by a weaker, but longer negative going excursion). Pulses can be applied in very rapid sequence, or a continuous wave can be modulated in a variety of ways. It is the firm proposition here that sonography does possess potential for primary and successful "stimulation" (pre-animation) of nerve cells. Thus, in combination, what we have here is the considerably enhanced ability and compatibility to control the four (4) major facets of successful neuron influence; that is to say, time allowed/allotment, shape of field, specificity of foci, and depth of induction. The full potential of ultrasound utilization relating to corrective brain treatment connected to rehabilitation of cognitive dysfunction pertaining specifically to early childhood development is being initiated here and now. EBA will have rejuvenating, habilitating, and rehabilitating effects on our most in need target population. Ultrasonic application, as a secondary complement to EBA, i.e., EBA/us, or primary (with potential initiation of EBA as secondary) will be an instrument of incomparable benefit to that same target population.

The abilities and possibilities of "ultrasonics" should not be underestimated. In addition to the medical field, the use of sound waves has found wide industrial use. As examples: for nondestructive testing, an object is irradiated with ultrasonic waves; variation in velocity or echo of the transmitted waves indicates a flaw. Fine machine parts, ball bearings, surgical instruments, and many other objects can be cleaned ultrasonically. They are placed in a liquid, e.g., a detergent solution or a solvent, into which ultrasonic waves are introduced. By a phenomenon called "cavitation", the vibrations cause large numbers of invisible bubbles to explode with great force on the surfaces of the objects. Film or dirt is thus removed even from normally inaccessible holes, cracks, and corners. Radioactive scale is similarly removed from nuclear reactor fuel and control rods. Again, in medicine ultrasonic devices are used to examine internal organs without surgery and are safer to genetic material than X rays. The waves with which the body is irradiated are reflected and refracted; these are recorded by a sonograph for use in diagnosis Metals can be welded together by placing their surfaces in contact with each other and irradiating the contact with ultrasound. The molecules are stimulated into rearranged crystalline form, making a permanent bond. Ultrasonic whistles, which cannot be heard by human beings, are audible to dogs and are used to summon them. And then let's not forget of course, sonography was first developed in World War II to locate submerged objects, i.e., sonar.

At this particular time it is not known (absolutely) whether ultrasound, as a primary inducer, may simply emit an electronic field which would be too weak for "exclusive/conclusive" brain habilitation animation. That is to say, the utilization of ultrasound wholly alone and separate with no adjunct instrumentation to complement at all. However, there is little doubt that as presented throughout this treatise, as an adjunct, as a secondary complementary instrumentation to EBA, and categorized in this presentation as EBA/us, sonography and/or ultrasound has remarkable probabilities within the spectrum of beginning treatment process. The ultrasonic pulsations would be able to specify locale, initiate the bringing of membrane potential to near threshold and then, after immediate follow-up integration with EBA, be of significant assistance in maintaining the smallest loci necessary for optimum goals and procedures conclusions. And of high enough import to bare often repeating, ultrasound is noninvasive, involves no radiation, and avoids multiple possible hazards such as bleeding, infection, or reactions to chemicals that plague numerous other diagnostic and treatment methodologies. This, again, is ideal when pertaining to EBA's chosen target population.

Continuing—further advantages of the invention, electromagnetic brain animation, include but are not limited to>(a) target population-infant, early childhood to adolescence. Several, but not all, reasons relate to>the fact that we now know cortical activity is different when viewing (SPECT/PET) topography of children with specific ongoing disabilities. The foci area may be significantly more pronounced and considerably more amenable to category formulation and/or reformulation due to a multiplicity of uniqueness related only to early developing brains. There seem also to be a number of additional, discernable and irregular manifestations in children who go through exhibitional phases of particular age pertinent impairments. (b) Particular and specific regions, but not all, able to be influenced by animation which pertain most specifically to mental difficulty would be the "amygdala"—storing painful and emotion-related memories; it also initiates memory storage in other brain regions. In other areas of the "limbic system"—indications are now strong that fear and/or anxiety can be quelled or diminished to a good extent by environmental influence and/or excitation of certain specific loci of that brain region. Attention Deficit or inability to pay attention for "normal" periods of time has recently been shown to relate directly to the "prefrontal cortex". There is also validated information pertaining to localized areas of the brain which impact such human manifestations as depression, bipolar disorder, dysthymia, boredom, decreased motivation, internal preoccupation, and irrational phobias, as well as many other negative consciousness expressions. A few other examples of brain region location connected with cognitive dysfunction within target population that could be amenable to electromagnetic brain animation (EBA)>the Frontal Lobe, associated with reasoning, speech, emotions, and problem solving—Parietal Lobe, associated with orientation and perception of stimuli—Temporal Lobe, associated with memory and also perception—and/or the Thalamus>where almost all sensory information enters first, then neurons send the information on to the overlying cortex. (c) Superposed magnetic fields from multiplicity 100+ mini-coils. There would be numerous advantages related to such a variety of fields coming from so many directions relating to the ability to influence neuron activity in mass as in contrast to singular strength. The results directly correlating to similar/superior patient conclusions utilizing less power/magnetic field aggression—being much more conducive with the target population. (d) Multiple variations in coil formulation, physicality, and/or structure/contour. This results in compound variations in strength and configuration of magnetic fields which are extremely beneficial toward differing possibilities of successful animation. (e) Current amplitude, pulse repetition rate, Hz gradient, i.e., all induction immersions controlled individually from outside, separate control box centers. This specificity of management heretofore not possible (f) "Cap" and/or hat-like instrumentation contained device fixated and stable on/over patient head wherein all coils (100+), directional formulations, multiple configurations, et al, are integrated as continual functioning particulars elevated off skull approximately minimum one half inch relating to moveable/flexible padded prong contact points integrating structure/architecture of cap/hat. (g) Cap/coils elevation from skull can be/is variable via adjustable prongs. This ability has positive impact on focus of magnetic fields. (h) Specific coil placement inside and target plotting precisely possible from multiple stated "cap" locations via coverage front to eye brow area, back to nape of neck, sides to top of ear level.

In accordance with the invention, terms to keep in mind and/or refer to throughout the electromagnetic patent application: "EBA mapping" is performed by changing coil/power and/or conductor position above and over the head while observing effects. This is accomplished via a separate control panel where all induction capsules within "Cap" are directly connected to individual control modules. "Multichannel EBA" refers to multiple (10 to 100 plus conductors/coils independently controlled). "Double EBA"—as in animation with two contact/coil/conductor points applied to different cerebral loci (same region) with timing and intensity adjusted separately. "Quadruple EBA" refers to 4 animation contact points with two or four different cerebral loci (singular region) and timing and intensity adjusted in quadrangle form or dual or individual as single. "Dual Multichannel EBA" as in up to 10 to 20 to 100 plus separate coils/conductors applications elevated over scalp/head with animation working independently from each point or any configuration of the multiplicity of points working in unison or gradient separations thereof. Also, in conjunction and/or collaboration,— "urEBA" refers to ultra rapid electromagnetic animation and "EBA/us" refers to electromagnetic brain animation utilized with ultrasound as a secondary complementary mechanism. "High frequency EBA" as in replication pulse rates above 1 Hz, "Low frequency EBA" as in replication rates below 1 Hz, and XLEBA refers to extra low as in a pulse rate, power source emission and conduction obtained from potential mobile 9V to 12V battery.

Specific instrumentation and/or services advantages include, but are not limited to,>>Acceptance incorporation of "animation" vs. forced merging of "stimulation". The upgrading and sophistication of "animation" is due to formulation of EBA's coagulation of multiplicity variation induction particles to>↑—amplify action, to encourage/to enliven, to influence, to animate—rather than—Stimulation>↓—to provoke, to frazzle, to manipulate, to act as a stimulant, i.e., to stimulate. The former (within context of brain organicity) relates to positivity; the latter to negativity. The upgrading and sophistication of "animation" is due to composition of EBA's "complex amalgamation" (multiple coil inductions/numerous locales/frequent variations/varied distance/rotating transmissions/multiple combined correlations thereof) excitation impetus toward assisting influence of target rather than singular more sharply rigorous induction toward forceful manipulation of same region. Besides this innovative montage, there is the added modernity of a curved (head contoured) conductive malleable plate situated against the inner top of the "cap" which can be utilized to connect and/or utilized two or more of the smaller coils transmission as one for a single stronger focused field in accord with the size of the combined coils. This comparatively mild current inducement via integration of inclusive EBA is considerably more attuned toward safety and success with intended locales of early childhood developing brains. In addition, due to potential "special care needs" of said population, EBA is an "adapter modality shifter". The "Thinking Cap" instrumentation, in total, has the capability to adjust connecting mechanisms to fit possible need for "extra low" output emissions (xLEBA). Power output, for example, can imitate from a simple 9V to 12V alkaline battery with such as pulse amplitude ranging from 1 to 80 Ma each channel and pulse frequency continuing to have a general scope of approximately 5 Hz to 100 Hz. AMS (adapter modality shifter) capability also includes inclusion of ultrasound as secondary device for cellular excitation preparation. This acronym is EBA/us.

In accordance with the invention, other acronyms and/or nomenclature necessary and/or helpful to know→"EMG" as in electromyography, recording of electrical activity associated with muscle movements. "XMEP" refers to extra-motor-evoked potential; an excitatory response to EBA. "8-shaped coil" refers to an animating coil with two planar wings with opposing current directions; induces a better focused electric field than a circular coil, Double-8/Quadruple-8 shaped coils associated only with EBA (exponentially greater capacity/multi-plexus focused fields electron pulsations). "Coil current" itself relates to the electromagnetic flow circulating in the coil formulation. "Current rise time" is the amount of time for current to proceed from zero to peak. "Electric field E" refers to nerves that are excited with E, which is induced by a changing B, hence, pulsed magnetic fields are needed for nervous excitation now referred to as "animation". "Magnetic field B"—the tissue is entirely transparent to B and hence the intensity of B does not describe the efficacy of animation; often about 2-3 tesla on the coil surface and 0.5 to 7-8 spread T in the cortex. Tesla (T) SI unit of magnetic flux density, Hz is measure=to one cycle per second, pulse amplitude=displacement from zero value or rest position to greatest distance (as in a wave—from center to greatest distance). The greater the distance the higher the energy, and Ramp Ma=equal modulation amplitude, i.e., maximum displacement from zero. An amp or ampere is simply an electrical measure of/or unit.

In accordance with invention, the general procedure includes passing irregular current from a structuralized "Thinking Cap" electromagnetic brain animation generator—consisting within—those (1 to 100+) conducting coils generating differing pulsating fields capable of inducing action/excitation within and among a chosen group of neurons. These varying electromagnetic fields are/can be multidirectional in inducing neuron animation. The pulses of current are generated with a circuit containing a discharge capacitor connected with these coils in series by a thyristor. With the capacitor first charged to 2-4 kV, the gating of the thyristor into the conducting state will cause the discharging of the capacitor (one or more within a large control box/panel) used to discharge the necessary "controlled" power to the coils. There may, if critical, be another thryistor (semiconductor switch capable of handling high peak currents in a short time) used for further control of surge going into multiple coils. This can, in addition, be utilized as a more sophisticated and/or back-up "control box" of all multiple coils from which pulses emanate. The electromagnetic brain animation may utilize several different pulse forms to effectuate the desired enhancement of already superior brain region plasticity. The pulse phase formulations range from mono to multi excitation that is applied to achieve the desired potential in a satisfactory/necessary percentage of nerve cells at the animation site. In one manifestation the pulse form can have a frequency of approximately 2-1000 Hz, but the frequency may be particularly useful in the range of approximately 60-200 Hz. There is expected to be usage at frequencies of approximately 50-100 Hz, 50-200 Hz, and 100-300 Hz. These pulses can start from each coil either individually or with opposed numbers at a time, from changeable locations within the "cap", examining cortical and/or all pertinent brain region processing, including sensory and cognitive functions. The basic chain of events, the induced E is strongest near the coil and typically stimulates a cortical area of a few centimeters in diameter. Fixated close to the skull, one half inch minimum above, inside said cap/hat like device, these pads (coils) are focused at singular and/or multiple varying parts (same regions) of brain biology relating to cognitive dysfunction and/or other human performance issues depending on the goal of treatment and/or research. Focus and/or specificity of induction/integration into neuron or cellular structure is improved or denigrated depending on distance from location being treated. With the multiplicity of coils and multiplicity of emanating direction variations, numerous cortical/or other areas can be simultaneously stimulated at multiples of the normal centimeter area. EBA pulses cause coherent firing of magnetic fields formulations in the animated area as well as altered multiple firings to synaptic input, i.e., neurotransmitter-receptor clusters. At microscopic levels, E affects the nerve cells' transport voltage across brain region membrane and thereby the voltage-sensitive ion channels.

Complementary brain imaging tools are used to detect the associated electrical currents and changes in blood flow of metabolism. If coils are too close to skull, magnetic field diffusion is more prominent. With rapid electromagnetic brain animation (rEBA) as well as ultra rapid electromagnetic brain animation (urEBA), excitation, i.e., animation can be/are applied to the same brain region (although much of the time will emanate from several different coils at once or in rapid sequence) multiple times per second—multiple consecutive seconds. All inclusive direct clinician control includes, but is not limited to incorporation of the "amount"/ number of animations per second, the strength of the animation, the length of the sequence of animations, the time between sequences, the total number of animation sequences, and the total amount of animation in a given session or to a given brain position. All of these differing measures can be varied basically at discretion of treatment team. In addition, focus and/or specificity of induction/integration into neuron or cellular structure is improved or denigrated depending on distance from location being treated. If coils are too close to skull, magnetic field diffusion is more prominent. Generally, in combination, the shape of the electric field induced in the tissue depends on 1) the shape of the induction coil, 2) the location and orientation of the coil with respect to the tissue, and 3) the electrical conductivity structure of the tissue. Thus, the multiple coils situated in unequal distances, in varying locations with a variety of unorthodox structure physicality can have a wide array of potential utilitarian configurations to choose from for interaction with brain part regions. Field shaping with multiple coils, i.e., EBA channeling, the excitation field can be more readily controlled by changing currents in the coils individually. Field shaping is equivocal to finding the optimal currents to release pertaining to the optimal desired field configuration at finding the optimal currents. Under contemporary standards, it is not feasible to generate the number of field shapes desired and/or required for optimal influence over specific and larger portions of the brain. However, with the heretofore inapplicable amount of coils now offered by electromagnetic brain animation (EBA), the field-shaping problem may not be fully resolved, but we are much closer to reaching that goal than would have otherwise been the case.

An additional specification of basic instrument physical description: A hard rubber and/or plastic (or other nonconductive material) size adjustable cap and/or helmet (combination flexible leather, rubber and plastic) that fits, with thin column like structures (prongs), fixated-hovering just over the top of human head. "Cap" is fitted with multiple scalp connecting conducting pads and/or electrodes/coils of varying shapes/sizes (up to 100+). Protruding from top of "cap" are equal number elongated, insulated electric conduction wires (each individually connected to separate coils inside cap) which immediately correlate into one large cable-like cord, approximately one half inch diameter, (approximately 15 to 20 feet in length) connected to at least two, possibly more, separate control boxes (at least one containing one or more capacitors) which transmit, manipulate, coordinate necessary power to the "Thinking Cap" into correlation of coils, sizes, numbers, and target configurations relating to magnetic field conclusions determined via separate control box/panel through skull and integrating within specific brain regions.

These electromagnetic charges/fields can/will emanate (depending on goal and necessity) from choice of either a mobile, battery base (approximately 9 to 12-20 volts—for numerous lower necessity conduction stipulating lower level/ grade coil composition and/or higher current) and/or a standard electrical source (up to 10-12 k volts—for multiple necessity higher conduction stipulating necessity for higher level/grade coil composition) or a direct additional source of power or combination thereof. There are a number of controls (up to 100+) available to direct the impulse current to multiple parts of the skull and into brain area—either together or separately. The EBA controls/modulation/commands (computer and/or standard manual/electronic panel/control directed setup) capability are all inclusive—adjust currency higher/lower, pulse modulation faster/slower, or steady non-modulating level, as well as controlling individual head contacts, specific section contacts, and/or all contacts.

Pertaining to all areas of electromagnetic brain animation, coil design must always be taken into account. Effective design is sometimes held back by the high amount of energy that has to be driven through the coil(s) in a very brief time. The intense sub-millisecond current pulses can cause strong expanding and compressing forces in the coil. Problems in areas such as power consumption and coil heating can be alleviated by reducing the coil's resistance, determined by the wire gauge and coil geometry. Both wire gauge and coil geometry pertaining to EBA allow considerable additional inclination toward reducing coil resistance and thus positive reduction in power consumption and over heating. For example, when the cross-sectional dimensions of the wire exceed 1 to 2 mm, the skin and proximity effects change the current distribution in the wire and may increase the direct current resistance significantly. Due to the variations in size, shape, composition, wiring configuration, and multiplicity of coils relating to EBA, this current resistance can/may remain at a level considerably lower than would be the current norm.

The current standard stimulating coils are either circular or 8-shaped. Electromagnetic brain animation (EBA) introduces several new coil shapes including "double 8s", triple bar circles", "dumbbells", "double squared triangles", "double rectangled squares", "elongated rectangles", "double circles within circles, as well as several others. It is well known that shape is crucial toward conclusion of magnetic fields; therefore, it is imperative that significant differentiation in coil configuration be an integral manifestation relating to any successful positive neuron influence. A typical induction heating system consists of the induction heating power supply, an induction heating coil, and a water-cooling source, which cools the coil and several internal components inside the power supply. The induction heating power supply sends alternating current through the induction coil, thus generating a magnetic field. When a work piece is placed within the coil and enters the magnetic field, eddy currents are induced within the work-piece, generating precise and localized heat without any physical contact between the induction coil and the work piece. Heretofore, the norm consisted essentially of two concentric coils with a common soft-iron core, a primary coil with relatively few windings of heavy wire, and a secondary coil with many turns of fine wire. Excitation of the primary coil by rapidly interrupted or variable current induces high voltage in the secondary coil. The primary differentiation (in this arena) of the EBA transformers relates to the multiple coil formulations, total number of coils available, and duality of coil power strata and source. These distinctions, of course, are all the difference. The coils can be/are made in many shapes and sizes to custom fit specific applications. The induction coil design is one of the most important aspects of an induction heating system. The coil is a custom design to give the work piece the proper heating pattern and maximize efficiency of the induction heating power supply. The coil cores may/do vary, as will other structure and coagulation when relating to the several differing coil types of EBA. This also is true of the considerable variation in process and methodology pertaining to the xLEBA (extra low electronic brain animation) generation.

Basic core/composition material usually is iron or sometimes copper. Under "standard" conditions, the cores are preferably constructed of a ferromagnetic material. They can have an outer diameter between approximately 2 and 7 inches, and an inner diameter between approximately 0.2 and 1.5 inches or even smaller. The material of the cores has a magnetic saturation of at least 0.5 Tesla, and preferably at least 1.5 Tesla, or even 3.0 Tesla or higher. In the ideal manifestation, the core conforms in construction to the shape, at least in accord with its size, of the head to improve its efficacy. There is a very recent investigation, ongoing at this time, looking into the possible use of a titanium based alloy. In addition, there is experimental talk pertaining to silicon carbide (SiC), i.e., in conjunction with polytype material with physical and electronic properties unmatched for high power, temperature tolerance, and device application. EBA would be/is adaptable to the continuum of optimal, utilitarian coil available. The "Thinking Cap" instrumentation, in total, has the capability to adjust connecting mechanisms to fit possible need for "extra low" output emissions (xLEBA). Power output, for example, can emanate from a simple 9V to 12V alkaline battery with such as pulse amplitude ranging from 1 to 80 Ma each channel and pulse frequency continuing to have a general scope of approximately 5 Hz to 100 Hz. This level of intensity output is not generally considered able to "reach" relevant brain areas. However, its intention is not for pinpoint targeting of specific neuron groups in order to habilitate, rehabilitate and/ or redirect as is norm criterion and practice EBA.

"Extra Low EBA" is generally meant solely for the purpose of brain and/or region "invigoration". The power induction is of such a low density as to be completely harmless to any and all early childhood age groups; but, at the same time, transmits enough intensity to "energize, enliven, revitalize" leading to mild animation. This can be a quite useful pre-classic EBA treatment modality relating to multiple investigatory as well as safety purposes. For example, a kind of temporary hyper-conductivity of the brains already approximately some 20 W of electrical current may be manifested. An increase in potential acceptability for higher success with archetypal EBA is a possibility. Or, it is long known that small increased inductions of electrical charges into the human brain can sometimes result in "psychic energizing"; that is to say, act as kind of an antidepressant. There are a myriad of, at least initial, potential implications within that particular arena. The only coils (or actually pads) necessary for these kinds of electrical transmission through the cranium would be something akin to attachable/detachable portable cloth, foam or carbon based silver coated pad/electrode devices. The power source would transmit through relevant (AMS) "adaptor modality shifter" wire conduction within the same inclusive cord/cable as utilized for EBA. The initial power relays would simply transfer to attachment on the lesser power source/ battery.

A clearly seminally primary separation of EBA from all other earlier forms of non-invasive impacting of the brain relate directly to its specificity of "target population". There is an unprecedented and more exciting allowance for successful, positive intervention into formulating/growing brain activity and either augmenting beneficial normalcy direction or rehabilitation of negative pathology than at any other time during human development. At this level, it does not need to undergo the much more arduous task of "rehabilitation" (restoration of aptitude, capabilities, a potential) because it has only just relatively begun early habilitation (initiation a building of original aptitude, capabilities, potential). In direct and specific correlation with this fact of the matter, brain development research tells us that one more step inside this optimum stage/phase presents two more momentous epochs; critical periods and sensitive periods. Understanding the difference is crucial for understanding the needs of the brain early in life and for understanding when and how electromagnetic brain animation (EBA) can most successfully intervene. For example, at birth, the human brain is still preparing for full operation. The neurons exist mostly apart from one another. The brain's task for the first 3 years is to establish and reinforce connections with other neurons. These connections are formed when impulses are sent and received between neurons. Axons send messages and dendrites receive them. These connections form synapses. Indications are that electromagnetic brain animation may be able to intercede relating to impulses sent and received when/if there may be an early suggestion of stunted habilitation of normal processes and/or a negative pathology formation.

Critical periods represent a narrow window of time during which the brain is most vulnerable to the absence of environmental influences or stimulation. Vision is a good example: Unless an infant sees light during the first 6 months, the nerves leading from the eye to the visual cortex of the brain that processes those signals will degenerate and die. Clinical psychological and neuroscience investigation tells us similar cause and effect takes place in relation to areas of the brain invigorated by societal and/or tactile influence or lack thereof. Many of the brain regions are, again, known and when target population individuals are diagnosed with social/ psychological dysfunction, EBA has the potential for optimum intervention which has been heretofore unavailable.

Sensitive periods are the broad windows of opportunity for certain types of learning. Sensitive periods represent a less precise and often longer period of time when skills, such as acquiring a second language, are influenced. But, if the opportunity for learning does not arise, these potential new skills are not lost forever. The skills acquired during sensitive periods are those that some people are better at than others. They include the social, emotional and mental characteristics that make us interesting people. The early brain research highlights birth through age 3 as a sensitive period for development and learning in all areas. This would also, obviously, be a most opportune time for primarily investigation and mapping of both normal and abnormal dynamics of cellular activity for comparative purposes and in addition, from ages 3 to 10-12 potential necessary integration of EBA pertaining to those emotional and mental characteristic that may be forming a negative pathology within our specific population.

A simplified synopsis of pragmatic process: A 10-year-old boy diagnosed with Dysthymia. >Pre interview—Sociologicals—Appropriate T-Battery-Previous topography—Preparation>Current SPECT/PET/MRI topography, by standard application, allows precise determination showing high probability locale of "frontal lobe" area (contributes to emotion)+hippocampus & amygdala for abnormal cortical activity. procedures>>if/when deemed appropriate, necessary, and/or more plausible, i.e., higher possibility for success—due to a multiplicity of variable factors relating to "target population"—previous to being prepared for electromagnetic brain animation and fitted with "The Thinking Cap" instrumentation>, initial ultrasound pretreatment "wave-frequency-induction" preparatory sonography procedure for optimum neuron sensitivity strata alignment. The application of the energy of ultrasonic waves vibrating at frequencies greater than 20,000 cycles per second, converted from electric current into high frequency pulsation beyond the range of human hearing. Specific chosen region is irradiated with reflection, refraction, and variation in velocity and/or echo of transmitted waves/wave patterns. Hippocampus and amygdala cellular structure, neuron cluster groupings begin observation recognition relating to initial influence and/or excitation via sonographic induction toward preparatory status for full EBA follow-up. Initial investigation and treatment completed. Process is wholly non-invasive, completely painless, and unequivocally without side effects. All necessary calibrations, data logging, readings, schematic overlay toward full therapeutic process. Patient fitted with "Thinking Cap"—electromagnetic brain animation (EBA) generator—architecturally elevated above and around head/skull, sits comfortably or lies down. Capacitor(s) dynamo electricity generation based via precedents 3000-5000 amps. Dual control panels—begin=lowest coil output-number-field generation, i.e., typical motor mapping via EBA, complementary mechanism's, and simultaneous targeting animation session consists of up to 100+ neural stimulatory animations at various positions on the head with multiple varying coil configurations. Distance from skull relates directly to less diffusion of magnetic field—aesthetic physicality of coil(s) relate directly to prominence and/or focus of animation. EBA delivery by passing brief (200-300 microsecond), strong (10,000-12000 volts, 6,000-8000 amps) electrical current through the multiple coils-multiple shape-multiple initiation locales placed adjacent to the head. The passage of electrical current induces a strong (2+Tesla) magnetic field which, in turn, induces electrical currents in nearby tissues. Integration compiled and "live" ongoing data determining, encompassing current driving modus to use, to shift, to alter slightly or sharply, EBA-10 coil iminations-2 areas region, xIEBA-25 coil iminations-5 differing physical coil configurations-5 areas region, rEBA-10 sequences-50 coil iminations-10 separate transmission locales-2 areas region-20 minutes, urEBA-100 individual coil iminations-20 separate areas region-five transmissions each area-vary each modulation each 5 cluster-gradient>power source 9V battery to 10,000V-current pulse 3 seconds to 300 microseconds—amps 80 to 8000-Hz 1 to 1000. Continual complementary tracking, comparison, investigation specific coil form and location with animation, results, conclusions, dynamics, lack thereof. Modulate multiplicity of controls in accordance. Results are utilizable "brain maps" (in conjunction with complementary mechanisms) allows specific initiation-continual pattern of inclusive emission necessity for highest positive outcome—depending on activity measurement. Ongoing targeting of induction into specific brain biology (BB) area by one up to 100+ individually controlled modulations (8-10-12 varying coagulations/assembly of degrees of inductions usually maximum needed/utilized) EBA Mapping modification a variations of frequency/rates—Adjust to control highest vantage constant measure of cortical excitability; observation/ investigation of integrity and efficacy of area to area scanning/ connections.—Continual disturbing of neuronal signal processing in the brain regions in order to find areas specific to task/goal. ↑ Vary frequencies appropriately ranging slow 1 Hz to rapid 30 Hz (still remains several orders of magnitude less than the brain's normal endemic metabolic power ranging around some 20 W). Specific Hz increases expected during ongoing application. Animation performance, live tracking of cellular responses, treat patient by targeting repetitive animation into calibrated and designated specific cortical areas. Verification of directional goals—20-30 minute sessions, average 2 sessions a week>6 weeks. Calibrate related cortical activity, frontal lobe, hippocampus, amygdala @ beginning-end sessions, + all other dysthymic indicators—2 neuro-consultants and consultations—determination alleviation and/or amplification gradient ¶ lack thereof. Post indicator appropriate testing 15-45 minutes after each treatment, larger T battery after each weekly treatment termination for standard comparative neurocognitive functioning, memory and learning. Testing every two week cycle reference depression/dysthymia and related mood states. Total of these allow determination of induction, gradient, direction, number of singular or multiple targeting as well as all other milieu reference EBA Referring to FIG. 1, a simulated view of the inside of an example EBA Thinking Cap which operates when positioned over a patient's head previous to treatment. There are 100 or more varying sized induction contact coils positioned for direct overhead and front/back, side/side neuron integration purposes of innovative proffered coils. In one example embodiment, three main coils include a dumbbell 15, double squared triangle 20, and triple bar circle 25 contours.

Referring to FIG. 2, an adjustable plate is situated inside the Thinking Cap top 30 and is positioned around the front, back, left and right sides. In operation, the plate is positioned one half to three quarters of an inch above the contacts/coils all around the skull area 35. The plate is a pliable conductive material about one sixteenth to one eighth inch in thickness bent in the basic underneath shape of the cap. One purpose is, by controlled contact, to be able to increase the emission field of two or more coils. Double ended arrows indicate an extended plate area. Circles indicate potential holes in the plate for coil contact areas.

Referring to FIG. 3, prongs 40 are moveable/adjustable, by the Thinking Cap is fixated and situated on the patient's head previous to treatment. There may be anywhere from 7 to 12 prongs. They are pliable and padded for comfort to the head. Adjustability distance of the coils from the skull 35 can range from one half to five inches.

FIG. 4 is an illustration of the phenomenon of directional specificity. A single coil at the vertex can stimulate tissue according to the direction. The image shows basic current flow in singularity with induced currents from one round coil hand-held above patient's head, very chaotic-quite non-specific and quasi-focus. This would be in considerable contrast to multi-emissions from a multiplicity of coil shapes via electromagnetic brain animation (EBA). Illustrated in FIG. 4 is: a single coil 45; primary current 50; secondary current 55; and direction of positive induction 60.

FIG. 5 shows multiple EBA coils in varying configurations. As shown here "dumbbell" (double squared with round holed center)—all emit a stronger, more utilizable electro-field than previous coils. The other coils are variations of the same advanced theme reference primary/secondary/preferred current direction. Illustrated coils are: dumbbell 65; square with hole 70; double figure eight 75; quadragon 80; and triple bar circle 85.

FIG. 6 summarizes the basic chain of events pertaining to general non-invasive processes. The induced E is strongest near the coil and typically stimulates a cortical area of a few centimeters in diameter. Pulsation causes coherent firing of magnetic field formulations in the animated area as well as altered multiple firing to synaptic input, i.e., neurotransmitter-receptor clusters. At microscopic level, E affects the nerve cells' transport voltage across brain region membrane and thereby the voltage-sensitive ion channels. Complementary brain imaging tools are used to detect the associated electrical currents and changes in blood flow of metabolism. With EBA, due to coil numbers, emission gradients, and configurations there would be exponential intra/extra variations throughout the procedure resulting in the animation coagulation.

FIG. 7 shows differentiation between early childhood development habituation and highest plasticity relating to critical time for peak window of opportunity pertaining to maximum success via EBA intervention assisting facilitation of neuron evolution. Generation is at its most sensitive to outside inducement relating to such as dendrites, spines, cell bodies, myelin sheaths, axons, synapses, i.e., the continuum of nerve construction.

Referring to FIG. 8, the ratio of the transverse and gradient field mechanisms is independent of the axon size. A schematic illustration of activation mechanisms and axon membrane polarization in a transverse field is shown for varying external applications of electric field patterns. The axon membrane polarization is sketched for different externally applied electric field patterns (arrows): (a) identical E down the axon, no variation from the resting status (b) gradient initiation (c) crooked axon in uniform E, depicting only the gradient activation; (d) transverse activation, with E locally across the axon; (e) axon concluding in uniform E. D and H signify depolarization and hyper-polarization, in that order. Implicit indication is then given that E is indistinguishable outside and inside the cells.

FIG. 9 are plots of focality in cm versus number of coils for different coil diameters and illustrates the use of multiple independently controlled animating coils. It has any number of advantages of over standard one coil or figure-of-eight coil stimulation. One can excite/animate numerous loci at the same time, or at delaying or varying times. With EBA, the operator can concentrate two or more coils at one locations and/or multiple locations with any number of cross configurations. In addition, the smaller the coils in combination with the multiplicity of coils relates directly to the size and specificity of the focality of animation induction. Below gives indication of smaller focal points directly correlated with size and number of coils.

FIG. 10 illustrates an outer view of the Thinking Cap. Shown are adjustable prongs, adjustable chin stability assistance, and other named parts of instrumentation relating to the ultrasound attachments. Validation of localized stimulation of active (nerve or cortical) tissue by ultrasonically induced electric fields relates directly toward analytical solutions that pertain to the field distribution which can be derived for an ideally collimated ultrasonic beam. As an example, an ion in a conducive medium, with charge q (this is in italics). The longitudinal particle motion of an ultrasonic wave with cause the ion to oscillate back and forth in the medium of velocity v. In the presence of a constant magnetic field, B(0) (this is subscript), the ion is subjected to the Lorentz force $F=qv \times B(0)$ (1) This produces an electric current density given by J(0) (this is subscript)$=n+u+=n.u.$)F. Illustrated are: a thinking cap cover or casing 90 which includes power relays to the coils; power transference conduit 95 to multiple coils; inclusive cable to main power 100; an ultrasound induction attachment 105.

FIG. 11 illustrates the initial treatment modality relating to EBA/US whereas ultrasonic waves vibrating at frequencies greater than 20,000 cycles per second are integrated through the human/patient's skull and into an excitation focal area (in this case the "limbic system" due to manifestation of "over-anxious disorder"). The sonographic induction causes initial 1st phase animation to enmesh targeted organicity bringing multiple neuron structure to hypersensitive pre-threshold status.

What I claim as my invention is:

1. A method for non-invasive excitation of specific brain neurons, comprising:
   projecting a combination of electromagnetic radiation and ultrasound pulses on to a specific area of a brain that is known to impact or result in precise emotional and/or mental difficulties;
   wherein the ultrasound pulses are initiated from a cap configured to conform to a human head;
   wherein the electromagnetic radiation is initiated from a plurality of coils connected to the cap; and
   wherein the combination of electromagnetic radiation and ultrasound induce cell or neuron depolarization for the purpose of enhancement, habituation, rehabilitation, and/or redirection of said abnormal mental difficulties.

2. A cap instrument configured to be placed in physical proximity to a human head, for causing neuron depolarization for ameliorating the effects of a mental disorder, the apparatus comprising:
   the cap instrument comprising:
   a plurality of coils arranged in rows on the cap configured to emit a rate of pulses of a electromagnetic radiation when energized with electric current, wherein the pulses have a pulse frequency; and
   an adjustment mechanism connected to the cap for adjusting the distance of the coils from the head for focusing the electromagnetic radiation into the head when the cap is worn by the head;
   an ultrasound attachment for generating ultrasonically induced electric fields within a brain; and
   wherein instrument is configured to emit pulses with a pulse frequency above 50 Hz.

3. A method for stimulating a specific area of a brain using an induction device, comprising:
   recording the spatial structure of the brain;
   generating a live (present time) model of the brain and specific regions via schematic screen combinations of topography;
   projecting a combination of electromagnetic radiation and ultrasound pulses on to a specific area of the brain that is known to impact or result in emotional or mental disorders;
   wherein the ultrasound pulses are initiated from a cap configured to conform to a human head;
   wherein the electromagnetic radiation is initiated from a plurality of coils connected to the cap; and
   wherein the combination of electromagnetic radiation and ultrasound induce cell or neuron depolarization for ameliorating mental disorders.

4. The method of claim 1, further comprising configuring the shapes of the coils to target a region of the brain.

5. A method for non-invasive excitation of specific brain neurons, comprising:
   preconditioning an area of the brain by targeting an ultrasound beam on to the area;
   projecting electromagnetic radiation pulses onto the area of the brain that is known to impact or result in emotional or mental disorders, wherein the radiation is emitted in a sequence of pulses, wherein the duration of each pulse in the sequence is less than 10 milliseconds and wherein the pulses in the sequence alternate in polarity; and
   post treating the area of the brain with an ultrasound beam;

wherein the combination of electromagnetic radiation and ultrasound induce cell or neuron depolarization for ameliorating mental disorders.

6. An apparatus for causing neuron depolarization for ameliorating the effects of a mental disorder, the apparatus comprising:
 a cap instrument configured to be placed in physical proximity to a human head, for comprising:
  a plurality of coils arranged in rows on the cap configured to emit a sequence of pulses of a electromagnetic radiation when energized with electric current, wherein the pulses have a pulse frequency; and
  an adjustment mechanism connected to the cap for adjusting the distance of the coils from the head for focusing the electromagnetic radiation into the head when the cap is worn by the head;
 an ultrasound attachment for generating ultrasonically induced electric fields within a brain; and
 wherein the pulse sequences comprise of a series of waves greater than 1000 amps in electrical current and less than 10,000 amps and the pulse sequences are in the range of 5-50 seconds in duration, wherein the combination results in having each wave between less than 1 millisecond in duration to 1 tenth of 1 millisecond in duration and the magnetic field produced thereby is at least 1 to 3 Tesla.

7. An apparatus for causing neuron depolarization for ameliorating the effects of a mental disorder, the apparatus comprising:
 a cap instrument configured to be placed in physical proximity to a human head, for comprising:
  a plurality of coils arranged in rows on the cap configured to emit a sequence of pulses of a electromagnetic radiation when energized with electric current, wherein the pulses have a pulse frequency; and
  an adjustment mechanism connected to the cap for adjusting the distance of the coils from the head for focusing the electromagnetic radiation into the head when the cap is worn by the head;
 an ultrasound attachment for generating ultrasonically induced electric fields within a brain; and
 wherein the pulses range from 5 seconds to 50 seconds in duration, and have a frequency that ranges from 10 Hz to 100 Hz.

8. An apparatus for causing neuron depolarization for ameliorating the effects of a mental disorder, the apparatus comprising:
 a cap instrument configured to be placed in physical proximity to a human head, for comprising:
  a plurality of coils arranged in rows on the cap configured to emit a sequence of pulses of a electromagnetic radiation when energized with electric current, wherein the pulses have a pulse frequency; and
  an adjustment mechanism connected to the cap for adjusting the distance of the coils from the head for focusing the electromagnetic radiation into the head when the cap is worn by the head;
 three congruent thyristor connections configured to consecutively or simultaneously operate to open and close power gap allotments;
 an ultrasound attachment for generating ultrasonically induced electric fields within a brain;
 wherein the pulses range from 50 microseconds to 400 microseconds in duration.

9. A method for treatment of depression, attention deficit disorder, anxiety, obsessive compulsive disorder, dysthymia, memory loss, learning disorder by directing a combination of electromagnetic radiation and ultrasound onto a specific area in the brain.

10. A method for non-invasive excitation of brain neurons of a person having a mental or emotional disorder, comprising:
 projecting a combination of electromagnetic radiation and ultrasound pulses on to specific areas of a brain that known to impact or result in mental or emotional disorders;
 wherein the ultrasound pulses are initiated from a cap configured to conform to a human head;
 wherein the electromagnetic radiation is initiated from a plurality of coils connected to the cap, the electromagnetic radiation varying in time and intensity from the plurality of coils and focused on a plurality of locations in the cerebrum;
 wherein the combination of electromagnetic radiation and ultrasound induce neuron depolarization for the purpose of rehabilitating the, and/or redirection of the mental or emotional disorder.

11. A method of treating a mental illness, comprising:
 applying an ultrasound beam to an affected area of the brain through a pathway;
 applying electromagnetic pulses through the pathway targeting the affected area of the brain, the electromagnetic pulses initiated from a cap structure surrounding the brain and positioned a fixed distance from the brain;
 wherein the method causes neuron depolarization at the affected area.

* * * * *